(12) United States Patent
O'Connor et al.

(10) Patent No.: US 7,668,604 B2
(45) Date of Patent: Feb. 23, 2010

(54) PACKAGING FOR MEDICAL PADS AND ELECTRODES

(75) Inventors: Rose M. O'Connor, Marcellus, NY (US); James C. Calenzo, Sr., Deerfield, NY (US); Arthur R. Eddy, Jr., Hampton, NH (US)

(73) Assignee: Conmed Corporation, Utica, NY (US)

( * ) Notice: Subject to any disclaimer, the term of this patent is extended or adjusted under 35 U.S.C. 154(b) by 682 days.

(21) Appl. No.: 10/869,565

(22) Filed: Jun. 16, 2004

(65) Prior Publication Data

US 2005/0283219 A1  Dec. 22, 2005

(51) Int. Cl.
*A61N 1/00* (2006.01)
(52) U.S. Cl. ..................................... 607/152
(58) Field of Classification Search ............... 607/115, 607/142, 148, 149, 152; 600/386, 391, 392
See application file for complete search history.

(56) References Cited

U.S. PATENT DOCUMENTS

| | | | |
|---|---|---|---|
| 3,670,736 A | 6/1972 | Panico | |
| 3,685,645 A | 8/1972 | Kawaguchi | |
| 3,702,613 A | 11/1972 | Panico et al. | |
| 3,762,420 A | 10/1973 | Moore et al. | |
| 3,826,245 A | 7/1974 | Funfstuck | |
| 4,034,854 A | 7/1977 | Bevilacqua | |
| 4,066,078 A | 1/1978 | Berg | |
| 4,177,817 A | 12/1979 | Bevilacqua | |
| 4,243,051 A | 1/1981 | Wittemann | |
| 4,353,373 A | 10/1982 | Sessions et al. | |
| 4,391,278 A | 7/1983 | Cahalan et al. | |
| 4,524,087 A | 6/1985 | Engel | |
| 4,610,254 A | 9/1986 | Morgan et al. | |
| 4,617,935 A | 10/1986 | Cartmell et al. | |
| 4,635,642 A | 1/1987 | Cartmell et al. | |
| 4,705,044 A | 11/1987 | Deluhery et al. | |
| 4,779,630 A | 10/1988 | Scharnberg et al. | |
| 4,798,208 A | 1/1989 | Faasse, Jr. | |
| 4,827,939 A | 5/1989 | Cartmell et al. | |
| 4,867,166 A | 9/1989 | Alexgaard et al. | |
| 4,955,381 A * | 9/1990 | Way et al. ................... 600/393 |
| 4,974,917 A | 12/1990 | Kornerup | |
| 4,979,517 A | 12/1990 | Grossman et al. | |
| 4,998,536 A | 3/1991 | Scharnberg | |
| 5,076,286 A | 12/1991 | Scharnberg | |
| 5,123,423 A | 6/1992 | Scharnberg | |
| 5,148,805 A | 9/1992 | Scharnberg | |
| 5,150,708 A | 9/1992 | Brooks | |

(Continued)

OTHER PUBLICATIONS

International Search Report for PCT/US2005/21987 Mailed Nov. 9, 2006 (10 pgs.).

*Primary Examiner*—George Manuel
(74) *Attorney, Agent, or Firm*—Marjama Muldoon Blasiak & Sullivan LLP

(57) ABSTRACT

Disposable biomedical pads include a conductive outer layer with an adhesive conductive protected layer on a major portion of the outer layer, with a double-sided release layer over the protected layer. Two pads are folded against each other, with the edges sealed to protect the gel layer from the environment. In use, the release layer is discarded, the gel layer placed against the skin, and in the case of defibrillation pads, the paddles are applied directly to the outer conductive layer. The outer layer serves as the packaging layer as well as the dispersive electrode.

24 Claims, 2 Drawing Sheets

U.S. PATENT DOCUMENTS

| | | | |
|---|---|---|---|
| 5,191,887 A * | 3/1993 | Cartmell | 600/392 |
| 5,203,330 A | 4/1993 | Schaefer et al. | |
| 5,254,109 A | 10/1993 | Smith et al. | |
| 5,402,884 A | 4/1995 | Gilman et al. | |
| 5,466,244 A | 11/1995 | Morgan | |
| 5,579,919 A | 12/1996 | Gilman et al. | |
| 5,645,571 A | 7/1997 | Olson et al. | |
| 5,697,955 A * | 12/1997 | Stolte | 607/5 |
| 5,827,184 A * | 10/1998 | Netherly et al. | 600/372 |
| 5,843,155 A | 12/1998 | Axelgaard | |
| 5,868,136 A | 2/1999 | Fox et al. | |
| 5,951,598 A | 9/1999 | Bishay et al. | |
| 5,984,102 A | 11/1999 | Tay | |
| 6,097,987 A | 8/2000 | Milani | |
| 6,115,625 A | 9/2000 | Heard et al. | |
| 6,115,638 A | 9/2000 | Groenke | |
| 6,223,088 B1 | 4/2001 | Scharnberg et al. | |
| 6,232,366 B1 | 5/2001 | Wang et al. | |
| 6,263,226 B1 | 7/2001 | Axelgaard et al. | |
| 6,272,385 B1 | 8/2001 | Bishay et al. | |
| 6,477,430 B1 | 11/2002 | Feuersanger et al. | |
| 6,993,395 B2 * | 1/2006 | Craige et al. | 607/142 |
| 2002/0156357 A1 | 10/2002 | Axelgaard | |
| 2003/0040788 A1 | 2/2003 | Dupelle et al. | |
| 2003/0055478 A1 | 3/2003 | Lyster et al. | |

\* cited by examiner

PACKAGING FOR MEDICAL PADS AND ELECTRODES

FIELD OF THE INVENTION

This invention relates generally to the field of packaging for biomedical pads and electrodes, and more particularly to those packages that protect an internal layer from the environment.

BACKGROUND OF THE INVENTION

Biomedical pads include various types of pads intended to be placed against a patient's skin. Typical biomedical pads include defibrillation pads, tab electrodes, EEG (electroencephalograph) pads, etc. In one example, defibrillation pads are employed in pairs, one for the positive voltage (anode), and one for the negative voltage (cathode). A basic defibrillation pad has an adhesive conductive gel on a foam layer, with the adhesive side being placed against the skin during defibrillation. The voltage is introduced directly into the conductive gel. A more advanced defibrillation pad is circular and rather large, i.e., with a 6" diameter, so as to provide ample surface for the current entering the patient's skin. An inner circular portion, the electrode portion, which is electrically linked to the voltage source, has the adhesive conductive gel on the inside. Looking at a cross-section of the defibrillation pad, the layers from the outside in are the foam layer, the electrode layer, the gel layer, and an optional release liner or layer. The entire defibrillation pad is packaged in foil to prevent the gel from drying out before use. The prior art is replete with variations of biomedical pads that are designed to overcome various limitations.

U.S. Pat. No. 6,263,226 discloses a multi-layer medical electrode that can be easily affixed to a conducting member.

U.S. Pat. No. 6,115,638 discloses a medical electrode system that includes a release liner which includes a pair of electrically non-conductive sheets with an electrically conductive sheet interposed between the two non-conductive sheets.

U.S. Pat. No. 5,466,244 discloses a pair of defibrillation electrodes that share the same flexible release liner surface.

U.S. Pat. No. 5,254,109 discloses two gel containing pads with a foil backing that are separable sealed in with a disposable barrier between them.

U.S. Pat. No. 4,779,630 discloses pair of defibrillator pads which have a conductive sheet that is attached to a defibrillator paddle, with a gel portion that is exposed by a peelable release liner.

U.S. Published Patent Application No. 2002/0156357 discloses a medical electrode with two gel layers and a porous, flexible electrically conductive release liner.

U.S. Pat. No. 6,477,430 discloses a paddle for use with a defibrillator with a detachable pad that has a flexible backing and a conductive gel portion.

U.S. Pat. No. 6,272,385 discloses a sealed defibrillator pad whose release line exposes a gel conductive portion that is placed on the skin of the patient.

U.S. Pat. No. 6,232,366 discloses a biomedical electrode with a conductive adhesive and flexible backing layer.

U.S. Pat. No. 6,223,088 discloses an electrode and a connector used in defibrillation are detachably connected to one another.

U.S. Pat. No. 6,115,625 discloses a medical electrode with a gel containing member and means for connection to an external electrical apparatus.

U.S. Pat. No. 6,097,987 discloses an external defibrillator electrode apparatus where the electrodes are coupled to the paddles of the defibrillator.

U.S. Pat. No. 5,984,102 discloses packaged medical electrodes for use with an electrometrical device that have a gel layer disposed on a base layer with the gel layers of the first and second electrodes in a facing relationship and separated by a common liner.

U.S. Pat. No. 5,951,598 discloses a defibrillator electrode system with a flexible backing member.

U.S. Pat. No. 5,868,136 discloses a medical electrode with a gel containing member and means for connection to an external electrical apparatus.

U.S. Pat. No. 5,843,155 discloses a flexible transcutaneous medical electrode.

U.S. Pat. No. 5,827,184 discloses a bioelectrode with a backing that is foldable about the middle.

U.S. Pat. No. 5,579,919 discloses packaged defibrillator pads with a gel conductive portion that share a common package.

U.S. Pat. No. 5,402,884 discloses packaged defibrillator pads with a gel conductive portion that share a common package.

U.S. Pat. No. 5,203,330 discloses disposable electrodes with a conductive foil backing and a gel interface.

U.S. Pat. No. 5,150,708 discloses an electrode for conducting current to the body with a flexible backing and a release liner that exposes a polymer gel.

U.S. Pat. No. 5,148,805 discloses a method for using a defibrillator pad system whereby a set of pad/electrodes is detachably connected to the defibrillator paddles.

U.S. Pat. No. 5,123,423 discloses a detachable defibrillator pad assembly and method of using same.

U.S. Pat. No. 5,076,286 discloses a method for using a defibrillator pad system whereby a set of pad/electrodes is detachably connected to the defibrillator paddles.

U.S. Pat. No. 4,998,536 discloses a method for using a defibrillator pad system whereby a set of pad/electrodes is detachably connected to the defibrillator paddles.

U.S. Pat. No. 4,979,517 discloses a disposable stimulation electrode suitable for placing in contact with a patient's skin with a flexible backing, a flexible tin plate that serves as a current receiving member from the defibrillation device and a conductive gel interface for contacting the skin.

U.S. Pat. No. 4,974,917 discloses an electrode plate for use with a defibrillator electrode.

U.S. Pat. No. 4,955,381 discloses a defibrillation pad with a foam backing, and a gel conductive portion that has a foil covering over the gel portion of the pad.

U.S. Pat. No. 4,867,166 discloses a flexible transcutaneous medical electrode.

U.S. Pat. No. 4,827,939 discloses a disposable medical electrode pad for application to the skin with a release liner that interfaces with a reusable electrical conductor.

U.S. Pat. No. 4,798,208 discloses a diagnostic electrode comprising a flexible foam backing, with a tin foil layer to which conductive gel is applied.

U.S. Pat. No. 4,705,044 discloses defibrillation paddle/electrodes that are reversibly coupled together.

U.S. Pat. No. 4,635,642 discloses a disposable medical electrode pad for application to the skin with a release liner that interfaces with a reusable electrical conductor.

U.S. Pat. No. 4,617,935 discloses a disposable medical electrode with a gel interface and a release liner.

U.S. Pat. No. 4,610,254 discloses a portable defibrillator with electrodes that are removably attached to the paddles.

U.S. Pat. No. 4,524,087 discloses a biomedical electrode with a conductive gel portion surrounded by a nonconductive portion, all on a flexible backing member.

U.S. Pat. No. 4,391,278 discloses a skin electrode with a flexible backing, a gel conductive portion, and an electrical contact means for interfacing with a monitoring/stimulating device.

U.S. Pat. No. 4,353,373 discloses an EKG electrode and package with a folded release liner.

U.S. Pat. No. 4,243,051 discloses a disposable transcutaneous electrode with a conductive adhesive and a conductive backing.

U.S. Pat. No. 4,177,817 discloses a dual terminal electrode for transcutaneous application of current with a foam backing and a conductive gel portion.

U.S. Pat. No. 4,066,078 discloses a disposable electrode with gel-skin interface and a conductive means for attaching the electrode to a stimulation device.

U.S. Pat. No. 4,034,854 discloses a packaged electrode with two electrodes with the gel portions arranged facing each other.

U.S. Pat. No. 3,826,245 discloses electrodes employing disposable electropads for cardiac instruments.

U.S. Pat. No. 3,762,420 discloses a defibrillation electrode comprising a conductive gauze with a metal backing that interfaces with a defibrillation paddle.

U.S. Pat. No. 3,702,613 discloses a device which houses and provides a conductive fluid to the interface between the operative surface of a defibrillator paddle and the surface or point of application to the human body.

U.S. Pat. No. 3,685,645 discloses a defibrillator electrode/package that accommodates two electrodes in facing relation to one another.

U.S. Pat. No. 3,670,736 discloses a device which houses and provides a conductive fluid to the interface between the operative surface of a defibrillator paddle and the surface or point of application to the human body.

U.S. Published Patent Application No. 2003/0055478 discloses a defibrillator electrode with a conductive foil layer next to a conductive gel liner.

U.S. Published Patent Application No. 2003/0040788 discloses a planar electrode for defibrillation with a release liner with a conductive gel surrounded by a non-conductive adhesive.

SUMMARY OF THE INVENTION

Briefly stated, disposable biomedical pads include a conductive outer layer with an adhesive conductive protected layer on a major portion of the outer layer, with a double-sided release layer over the protected layer. Two pads are folded against each other, with the edges sealed to protect the gel layer from the environment. In use, the release layer is discarded, the gel layer placed against the skin, and in the case of defibrillation pads, the paddles are applied directly to the outer conductive layer. The outer layer serves as the packaging layer as well as the dispersive electrode.

According to an embodiment of the invention, a medical pad unit includes first and second sections, wherein each section includes an outer layer, a protected layer overlaying at least a major portion of the outer layer; the outer layer being impermeable to air and moisture; the first and second sections being folded against each other such that an edge portion of the protected layers are touching; and the outer layers of the first and section sections are sealed to each other along the edge portion of the outer layers.

According to an embodiment of the invention, a medical pad unit includes first and second sections, wherein each section includes an outer layer, a protected layer overlaying at least a major portion of the outer layer, and a release layer overlaying at least the protected layer; the outer layer being impermeable to air and moisture; the first and second sections being folded against each other such that the release layers are touching; and the release layers of the first and section sections are sealed to each other along an edge portion of the release layers.

According to an embodiment of the invention, a medical pad package includes a sheet of a material which is impermeable to air and moisture; the sheet including first and second sections separated by a fold line; a protected coating disposed in at least one first location on the first section and in a corresponding at least one second location on the second section; a double-sided release layer disposed over each of the protected coatings; the first section being folded along the fold line over the second section, such that an edge portion of the first section of the sheet touches an edge portion of the second section of the sheet; and the edge portion of the first section is sealed to the edge portion of the second section.

DETAILED DESCRIPTION OF THE PREFERRED EMBODIMENT

Figure 1:
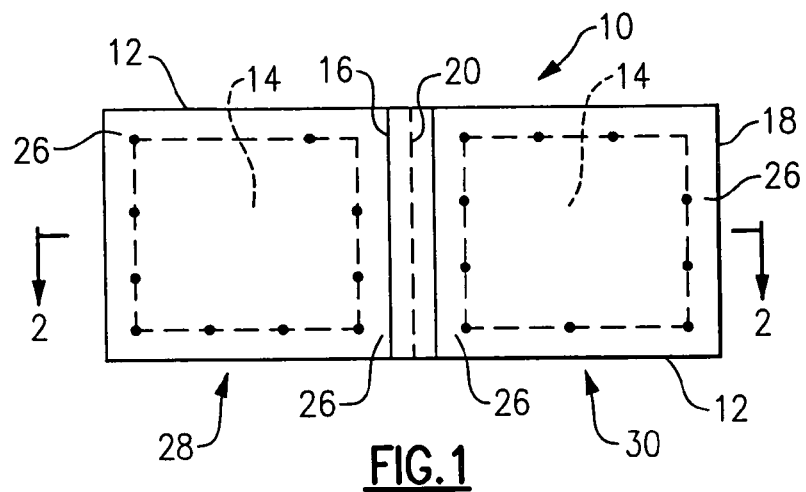
FIG. 1 shows a top view of a biomedical pad unit according to an embodiment of the invention.

Referring to FIG. 1, a biomedical pad unit 10 of the present invention includes an outer layer 12, which is preferably an electrically conductive layer and more preferably a metallic foil layer, although electrically conductive plastic would be preferred for applications requiring x-ray transparence or translucence. Outer layer 12 provides electrical conductivity in those applications which need it as well as being a protective outside barrier for the inner layers of unit 10. Outer layer 12 includes an outer side which is preferably suitable for printing images (symbology), patent number, brand name, instructions, etc. where a user can see and read it. When outer layer 12 is conductive, it serves as part of the biomedical pad unit itself, e.g., as with a pair of defibrillation pads.

Figure 2A:
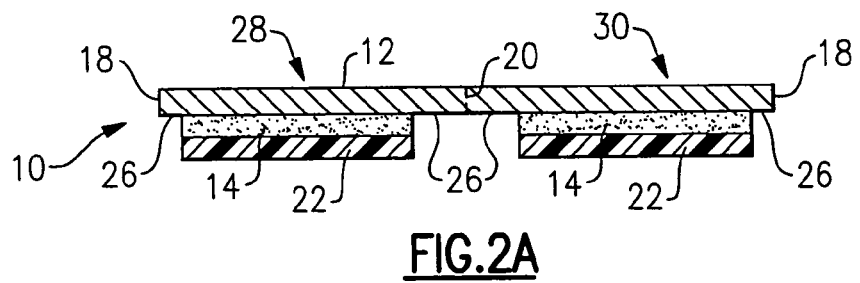
FIG. 2A shows a cross-sectional view along the line 2-2 of FIG. 1 of an embodiment of the invention.

A protected layer 14 is disposed in two locations on an underside of outer layer 12. Protected layer 14 is of a material that needs to be protected from the environment, which is accomplished on one side by outer layer 12, and on another side by an optional release layer 22 (FIG. 2A). For example, in a defibrillation pad, protected layer 14 is a conductive adhesive gel which must be prevented from drying out before use. In the embodiment shown in FIG. 2A, protected layer 14 does not interface with all of outer layer 12 but leaves a sealing area 26 for sealing or closure between the outside edges of outer layer 12, shown, for example, as a sealing portion or a sealing edge 18. At a minimum, each part of unit 10 preferably includes the combination of outer layer 12, protected layer 14, and release layer 22.

Unit 10 includes at least two sections 28, 30 which are connected by a fold line 20 which is optionally perforated to facilitate opening the sealed package. Fold line 20 is preferably stamped or pressed into outer layer 12. If more than two sections are in the total package, the sections can be arranged in either rows or columns. Sections 28, 30 are folded over fold line 20 on to one another so that at least either release layers 22 of each unit 10 or outer layers 12 of each unit are touching. If release layers 22 are not coextensive with the outer layers 12, then the sealing areas 26 of outer layers 12 of each unit 10 are touching. Sealing areas 26 are then sealed together to fully seal unit 10. The sealing can be done using adhesive, heat sealing, etc.

Because sections 28, 30 are folded on to one another so that at least the release layers, if present, of each unit are touching, the design permits a single, shared, release layer between the functional inner layers. If the release layers are absent, then the functional inner layers of each unit are touching. If the release layers are present but are not coextensive with the functional outer layers, then the sealing areas of the functional outer layers of each unit are touching.

When used as defibrillation pads, unit 10 is opened, sections 28, 30 are separated, release layer(s) 22 is removed, and sections 28, 30 are then placed in the proper locations on a patient. Defibrillation paddles are applied directly to outer layer 12 of each section 28, 30 since outer layer 12 is conductive. The current travels from outer layer 12 through protected layer 14, which in a defibrillation pad is a conductive adhesive gel, and onto the skin of the patient. Outer layer 12 acts as both the packaging layer and the conductive electrode layer as are found in the prior art.

Figure 2B:
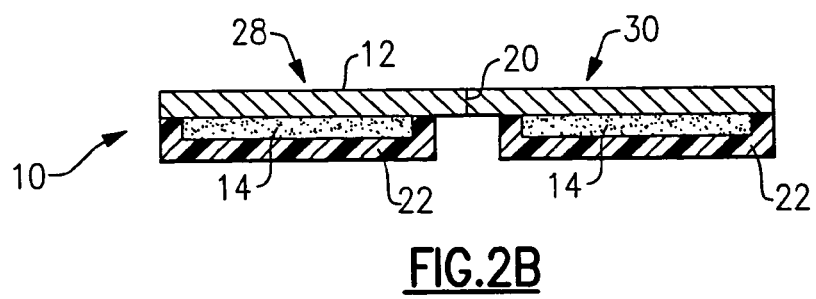
FIG. 2B shows a cross-sectional view along the line 2-2 of FIG. 1 of an embodiment of the invention.
Figure 2C:
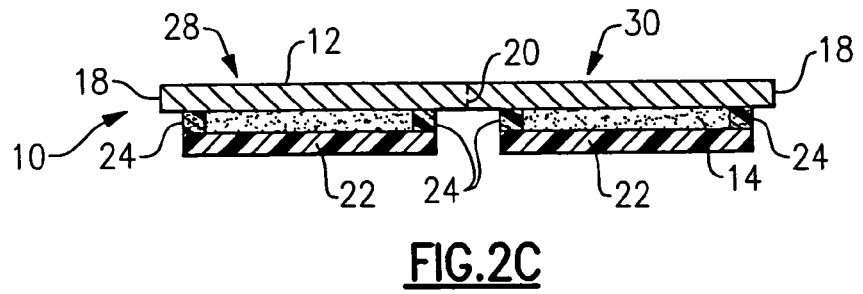
FIG. 2C shows a cross-sectional view along the line 2-2 of FIG. 1 of an embodiment of the invention.

Referring to FIGS. 2A-2C, release layer 22 is either coextensive with protected layer 14 as shown in FIG. 2A or possibly extends past protected layer 14 or even be coextensive with outer layer 12 as shown in the embodiment of FIG. 2B. Release layer 22 acts as a protective barrier or separation between protected layer 14 and an optional second functional inner layer (not shown) or some other material. The embodiment of FIG. 2C shows a border 24 surrounding protected layer 14 with release layer 22 covering both protected layer 14 and border 24. Border 24 can be of foam or dielectric material, either with or without an adhesive layer on it depending on the application.

Figure 3A:
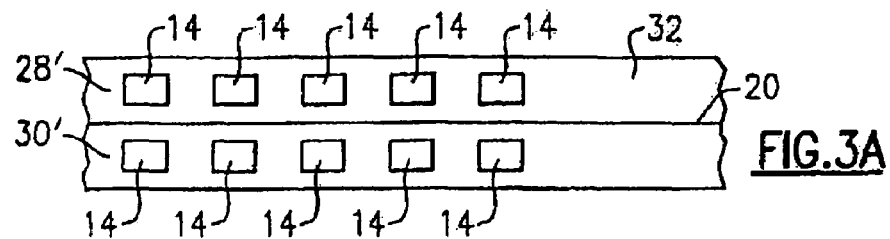
FIG. 3A shows a top view of a stage in the manufacturing process of a biomedical pad unit according to an embodiment of the invention.
Figure 3B:
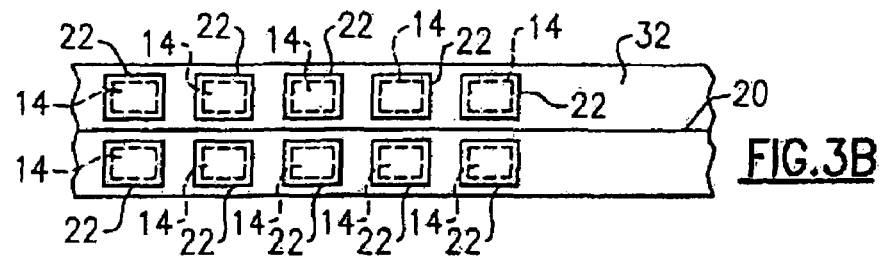
FIG. 3B shows a top view of a stage in the manufacturing process of a biomedical pad unit according to an embodiment of the invention.
Figure 3C:
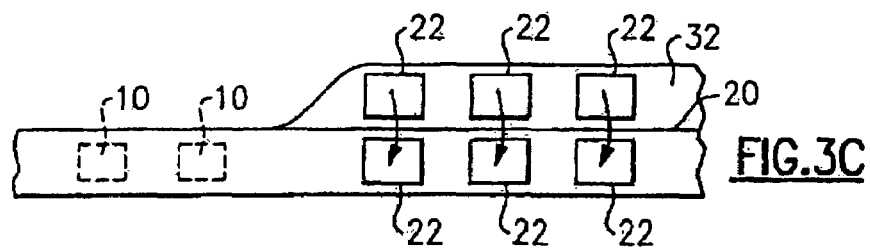
FIG. 3C shows a top view of a stage in the manufacturing process of a biomedical pad unit according to an embodiment of the invention.
Figure 3D:
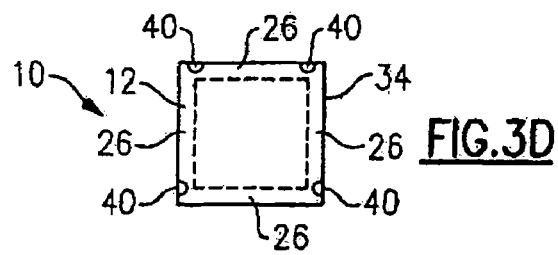
FIG. 3D shows a defibrillation pad package according to an embodiment of the present invention.

Referring to FIGS. 3A-3D, various stages in the manufacturing process of a biomedical pad unit according to an embodiment of the invention are shown. In FIG. 3A, a sheet 32 of preferably printed foil rollstock is run on an autoline, with the printed side down. The printing can include directions or symbology, and in the embodiment of a set of defibrillation pads, preferably includes a square indicating correct paddle placement for defibrillation. A slab of conductive gel 14 is laminated in an island format lengthwise along sheet 32, with the slabs preferably being deposited two-up on first and second sections 28', 30' as shown in FIG. 3A. A piece of double-sided release liner (release layer 22), i.e. release liner which preferably has silicone on both sides, which is slightly larger than slabs of conductive gel 14 is placed on each slab as shown in FIG. 3B. First section 28' is folded over onto second section 30' as shown in FIG. 3C, after which the foil layers 12 of folded first and second sections 28', 30' of a defibrillation pad package 34 are die cut, with package 34 then being sent to a package sealer for sealing on all four edge portions 26. All corners are preferably notched with notches 40 to enable a user to rip the sealed edges off pad package 34 to expose the two conductive gel slabs.

Figure 3E:
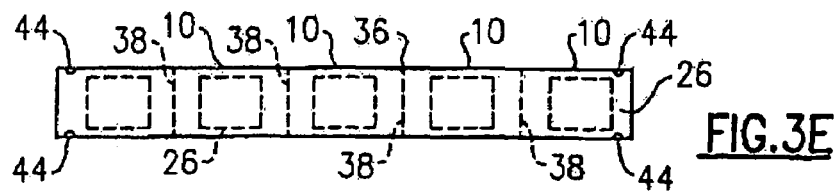
FIG. 3E shows a tab electrode pad package according to an embodiment of the present invention.

Referring to FIG. 3E, a tab electrode package 36 preferably includes a set of five units 10 which are preferably separated by perforations 38. A plurality of notches 44 optionally are placed within sealing areas 26 to aid the user in opening package 36. An alternative embodiment includes a plurality of packages 36 on a single roll instead of being grouped in quantities of ten.

Figure 4A:
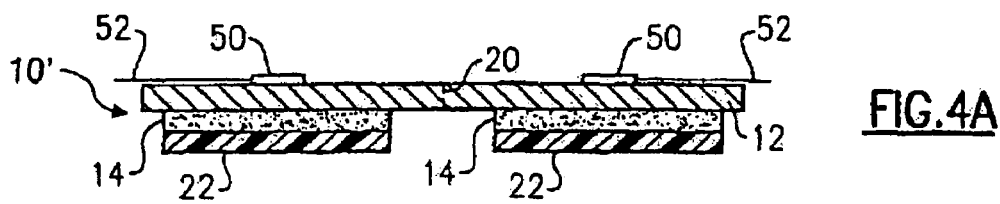
FIG. 4A shows a cross-sectional view of a defibrillation pad according to an embodiment of the invention.
Figure 4B:
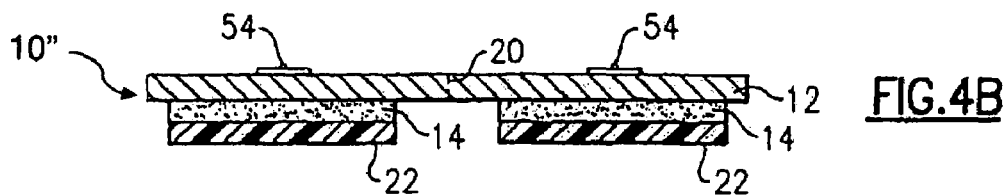
FIG. 4B shows a cross-sectional view of a defibrillation pad according to an embodiment of the invention.

Referring to FIG. 4A, a biomedical pad unit 10' is shown according to an embodiment of the invention in which an electrically conductive electrode 50 is fastened to outer layer 12. An electrical lead 52 is connected to electrode 50 for connection with an apparatus such as a defibrillation energy source. Electrode 50 is preferably connected to outer layer 12 using a conductive fastener, such as a metal or electrically conductive plastic rivet (not shown). In FIG. 4B, a biomedical pad unit 10" according to an embodiment of the invention is shown in which a snap electrode 54 is connected to outer layer 12, again preferably using a conductive fastener. Snap electrode 54 permits connecting a snap-connector type power cord as is known in the art. Both electrode 50 and snap electrode 54 are preferably disposed in a central location on outer layer 12 to facilitate efficient transfer of electrical energy and/or signals through the biomedical pad unit to and/or from the patient's skin.

While the present invention has been described with reference to a particular preferred embodiment and the accompanying drawings, it will be understood by those skilled in the art that the invention is not limited to the preferred embodiment and that various modifications and the like could be made thereto without departing from the scope of the invention as defined in the following claims.

What is claimed is:

1. A medical pad unit, comprising:
a first section including a first electrically conductive outer layer impermeable to air and moisture and a first protected layer overlaying at least a major central portion of said first outer layer and exposing an outer perimeter of the first electrically conductive outer layer; and
a second section including a second electrically conductive outer layer impermeable to air and moisture and a second protected layer overlaying at least a major central portion of said second outer layer and exposing an outer perimeter of the second electrically conductive outer layer;
wherein said first section and said second section are folded against each other such that an exposed perimeter portion of said first protected layer touches an edge portion of said second protected layer; and
said exposed perimeter of the first electrically conductive outer layer of said first section and said exposed perimeter of the second electrically conductive outer layer of said second section are sealed to each other to protect the first protected layer and second protected layer from the environment.

2. A medical pad unit according to claim 1, further comprising a double-sided release layer overlaying each of said protected layers.

3. A medical pad unit according to claim 1, further comprising a double-sided release layer overlaying at least one of said protected layers.

4. A medical pad unit according to claim 3, wherein said release layer overlays at least part of said outer layers not overlain by at least one of said protected layers.

5. A medical pad unit according to claim 3, further comprising a border overlaying a part of said outer layers which is not overlain by at least one of said protected layers, wherein said release layer overlays said border.

6. A medical pad unit according to claim 5, wherein said border is of a dielectric material.

7. A medical pad unit according to claim 3, further comprising a fold line in said outer layers separating said first and second sections from each other.

8. A medical pad unit according to claim 7, further comprising a plurality of perforations in said fold line.

9. A medical pad unit according to claim 3, further comprising a plurality of perforations in said outer layers separating said first and second sections from each other.

10. A medical pad unit according to claim 3, wherein at least one of said protected layers is an adhesive conductive gel.

11. A medical pad unit according to claim 1, wherein at least one of said protected layers is an adhesive conductive gel.

12. A medical pad unit according to claim 11, wherein said medical pad unit is a defibrillation pad unit.

13. A medical pad unit according to claim 11, wherein said medical pad unit is a tab electrode unit.

14. A medical pad unit according to claim 1, wherein said exposed perimeter portions of said outer layers are sealed by an adhesive.

15. A medical pad unit according to claim 1, wherein said exposed perimeter portions of said outer layers are heat-sealed.

16. A medical pad unit according to claim 1, further comprising an electrode fastened to an outside of said outer layers.

17. A medical pad unit, comprising:
a first section including a first electrically conductive outer layer having a length and a width, said outer layer impermeable to air and moisture and a first protected layer overlaying at least a major portion of said first outer layer, and a first release layer overlaying at least said first protected layer, said release layer having a length and a width greater than the length and width of said first outer layer and a perimeter edge; and
a second section including a second electrically conductive outer layer having a length and a width, said outer layer impermeable to air and moisture and a second protected layer overlaying at least a major portion of said second outer layer, and a second release layer overlaying at least said second protected layer, said release layer having a length and a width greater than the length and width of said second outer layer and a perimeter edge;
wherein said first section and said second section are folded against each other such that said perimeter edge of the first release layer touches said perimeter edge of the second release layer; and
said perimeter edge of the first release layer and said perimeter edge of the second release layer of said second section are sealed to each other to protect the first protected layer and second protected layer from the environment.

18. A medical pad unit according to claim 17, wherein said edge portions of said release layers are sealed by an adhesive.

19. A medical pad unit according to claim 17, wherein said edge portions of said release layers are heat-sealed.

20. A medical pad package, comprising:
an electrically conductive sheet of a material which is impermeable to air and moisture;
said sheet including first and second sections separated by a fold line;
a first protected layer centrally disposed on a portion of said first section and defining an exposed edge of said first section; a second protected layer centrally disposed on a portion of said second section and defining an exposed edge of said second section;
a double-sided release layer disposed over each of said protected coatings;
said first section being folded along said fold line over said second section, such that the edge portion of said first section of said sheet touches the edge portion of said second section of said sheet; and
said edge portion of said first section being sealed to said edge portion of said second section to protect the first protected layer and the second protected layer from the environment.

21. A medical pad package according to claim 20, wherein a number of each of said first and second locations is one, and said medical pad package contains two defibrillation pads.

22. A medical pad package according to claim 21, further comprising first and second electrodes fastened to said electrically conductive material on an opposite side of said material from said first and second locations, respectively.

23. A medical pad package according to claim 20, wherein a number of each of said first and second locations is five, and said medical pad package contains ten tab electrodes.

24. A medical pad package according to claim 23, further comprising five electrodes fastened to said electrically conductive material on an opposite side of said material from said five first locations, and comprising five electrodes fastened to said electrically conductive material on an opposite side of said material from said five second locations.

* * * * *